(12) United States Patent
Heesch

(10) Patent No.: US 10,661,056 B1
(45) Date of Patent: May 26, 2020

(54) GUIDE CATHETER SUPPORT INSTRUMENT

(76) Inventor: Christian M. Heesch, Spanish Fort, AL (US)

( * ) Notice: Subject to any disclaimer, the term of this patent is extended or adjusted under 35 U.S.C. 154(b) by 228 days.

(21) Appl. No.: 13/458,546

(22) Filed: Apr. 27, 2012

Related U.S. Application Data

(60) Provisional application No. 61/634,191, filed on Feb. 24, 2012.

(51) Int. Cl.
*A61M 25/00* (2006.01)
*A61M 25/01* (2006.01)

(52) U.S. Cl.
CPC ...... *A61M 25/008* (2013.01); *A61M 25/0041* (2013.01); *A61M 25/0054* (2013.01); *A61M 25/0074* (2013.01); *A61M 25/0102* (2013.01); *A61M 2025/0059* (2013.01)

(58) Field of Classification Search
CPC .... A61B 2017/3484; A61B 2017/3488; A61B 5/6869; A61B 2018/00351; A61J 15/0046; A61M 25/04; A61M 29/00; A61M 25/0074; A61M 2025/0079; A61M 2210/125; A61M 2210/127; A61M 2025/0293
USPC .................. 604/104, 105, 107, 175; 606/198
See application file for complete search history.

(56) References Cited

U.S. PATENT DOCUMENTS

| | | | |
|---|---|---|---|
| 3,568,659 A * | 3/1971 | Karnegis | 600/18 |
| 4,748,982 A | 6/1988 | Horzewski et al. | |
| 4,781,682 A | 11/1988 | Patel | |
| 4,813,930 A | 3/1989 | Elliott | |
| 5,098,412 A | 3/1992 | Shiu | |
| 5,263,963 A | 11/1993 | Garrison et al. | |
| 5,306,261 A | 4/1994 | Alliger et al. | |
| 5,336,184 A | 8/1994 | Teirstein | |
| 5,365,943 A | 11/1994 | Jansen | |
| 5,443,456 A | 8/1995 | Alliger et al. | |
| 5,456,667 A | 10/1995 | Ham et al. | |
| 5,681,280 A | 10/1997 | Rusk et al. | |
| 5,728,066 A * | 3/1998 | Daneshvar | A61M 25/10 604/113 |
| 5,733,248 A | 3/1998 | Adams et al. | |
| 5,769,821 A * | 6/1998 | Abrahamson | A61M 25/04 604/104 |
| 5,776,096 A | 7/1998 | Fields | |
| 5,820,592 A | 10/1998 | Hammerslag | |
| 5,868,733 A * | 2/1999 | Ockuly | A61M 25/0041 604/164.03 |
| 5,868,778 A * | 2/1999 | Gershony et al. | 606/194 |
| 5,885,259 A | 3/1999 | Berg | |
| 5,941,872 A | 8/1999 | Berg | |
| 5,984,878 A | 11/1999 | Engelson | |
| 6,083,213 A | 7/2000 | Voda | |

(Continued)

*Primary Examiner* — Kami A Bosworth
(74) *Attorney, Agent, or Firm* — Cara C. Morris

(57) ABSTRACT

One embodiment provides a support catheter member assembly, preferably for cardiac interventional procedures, comprising an elongated tubular body having proximal and distal ends, and a plurality of lumina extending axially therethrough. A plurality of support members extend through the catheter, exit at a defined distance from its distal opening, and reattach at its distal end. Manipulation of support members leads to their flexing outward/retraction towards the catheter, providing an adjustable support assembly with which the position of a separate guide catheter can be stabilized.

10 Claims, 10 Drawing Sheets

(56) References Cited

U.S. PATENT DOCUMENTS

| | | | |
|---|---|---|---|
| 6,190,379 B1 * | 2/2001 | Heuser et al. | 606/28 |
| 6,350,252 B2 | 2/2002 | Ray et al. | |
| 6,595,952 B2 | 7/2003 | Forsberg | |
| 6,645,160 B1 | 11/2003 | Heesch | |
| 6,860,876 B2 | 3/2005 | Chen | |
| 7,344,515 B2 * | 3/2008 | Coyle | A61M 25/0082 604/104 |
| 7,497,853 B2 | 3/2009 | Fischer et al. | |
| 7,717,899 B2 | 5/2010 | Bowe et al. | |
| 7,993,303 B2 | 8/2011 | Von Oepen et al. | |
| 8,133,213 B2 * | 3/2012 | Lashinski | A61F 2/2418 604/104 |
| 2001/0044591 A1 * | 11/2001 | Stevens | A61M 1/3659 604/6.11 |
| 2004/0225354 A1 * | 11/2004 | Allen et al. | 623/2.11 |
| 2006/0167437 A1 * | 7/2006 | Valencia | A61M 25/00 604/523 |
| 2007/0149995 A1 * | 6/2007 | Quinn | A61B 17/12122 606/194 |
| 2012/0109155 A1 * | 5/2012 | Robinson | A61B 17/0401 606/139 |

* cited by examiner

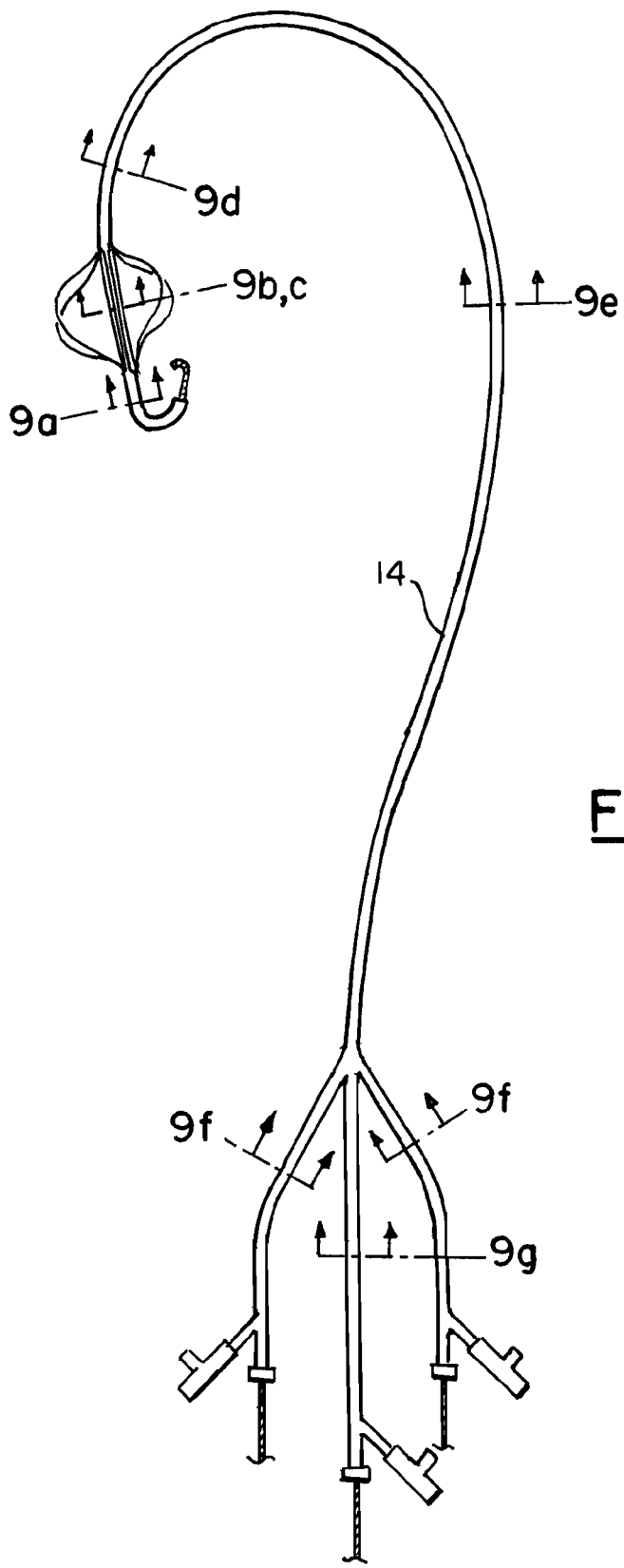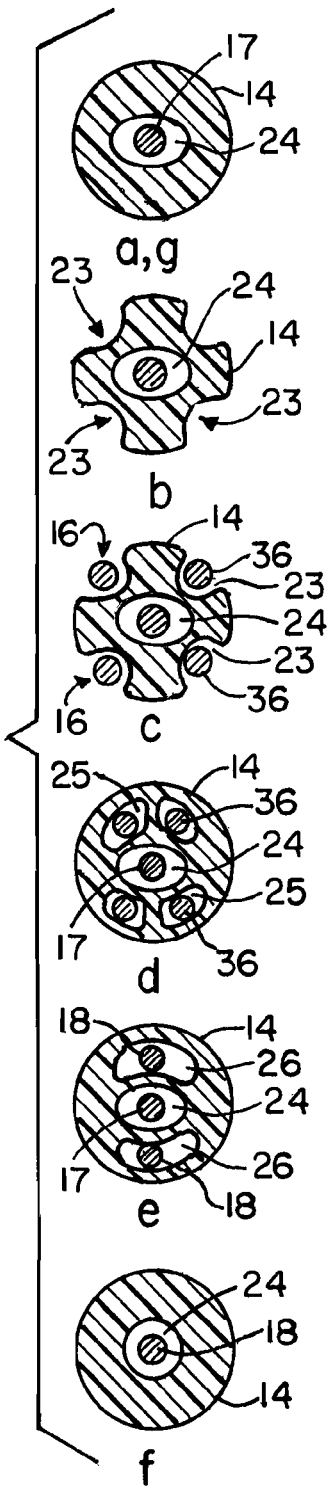
FIG. 8.
FIG. 9.

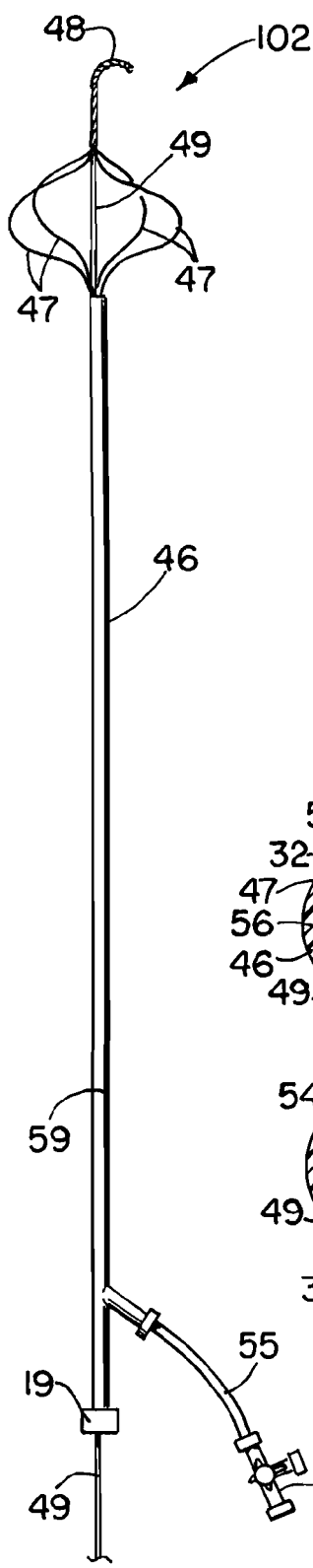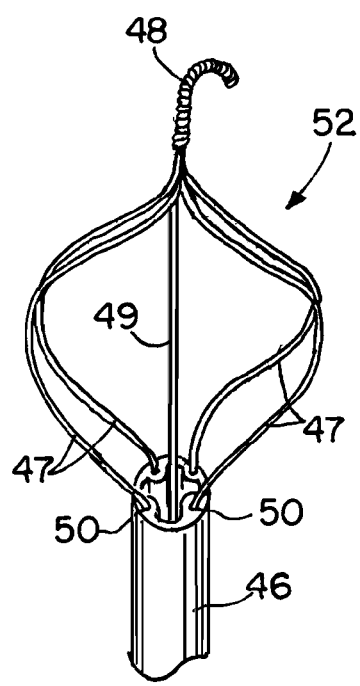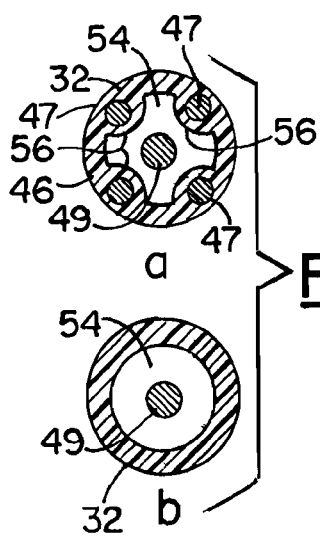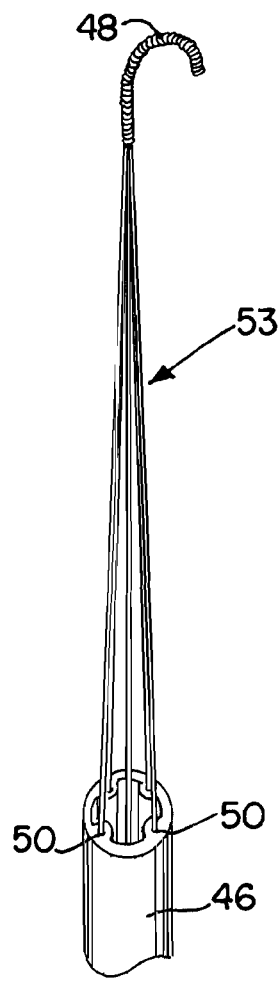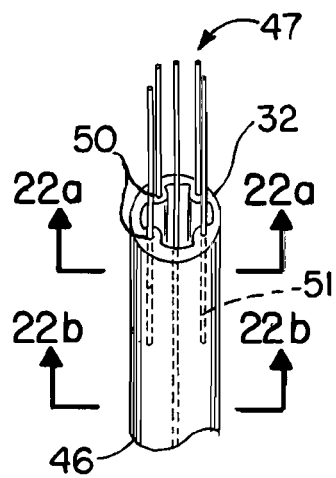
FIG. 19.
FIG. 20.
FIG. 21.
FIG. 22.
FIG. 23.

GUIDE CATHETER SUPPORT INSTRUMENT

CROSS-REFERENCE TO RELATED APPLICATIONS

This is a non provisional patent application of U.S. Provisional Patent Application Ser. No. 61/634,191, filed Feb. 24, 2012.

Priority of U.S. Provisional Patent Application Ser. No. 61/634,191, filed Feb. 24, 2012, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to guide catheters for coronary or peripheral interventions. More particularly, the present invention relates to an improved cardiac catheter apparatus that includes a first catheter (a guide catheter) and second catheter that is specifically configured to function as a support member for the first catheter.

2. General Background of the Invention

During percutaneous coronary or peripheral vascular intervention procedures, guide catheters are advanced from the periphery, usually the femoral or radial arteries, towards the vascular territory of interest. For a coronary intervention, the tip of the guide catheter is positioned in the ostium of the coronary artery to be treated. Subsequently, wires, balloons, stents and other equipment are advanced into the selected coronary artery in an attempt to clear up atherosclerotic blockages (stenoses) and improve coronary circulation.

One of the most feared technical challenges encountered by the operator is the lack of guide support. Modern guide catheters, through which the interventional devices are delivered into the coronary arteries, are designed to be small in diameter to limit the size of the puncture injury at the site of their insertion into the arterial system. The disadvantage of such small diameter is that modern guide catheters are often not sufficiently rigid to allow the operator to force the interventional equipment across highly stenotic (blocked) lesions in the coronary artery, owing to resistance offered by the obstructive material to the advancing equipment. Such resistance tends to be especially significant if blockages encountered are total, occlude 100% of the lumen of the artery, are calcified and/or long, or if the equipment to be advanced is inflexible and bulky. If the operator, in such situations, attempts to force his equipment into the coronary artery, the lack of rigidity of the guide catheter often leads to the catheter being pushed out of its position of engagement with the coronary ostium, a problem referred to as 'lack of guide support'. Inadvertent disengagement can have potentially catastrophic consequences, most notably loss of guide wire position across the stenosis and sudden total closure of the latter.

Many strategies have been described to deal with such guide problems while leaving the current equipment in place, yet they involve, at best, prolonged efforts often using additional equipment. Frequently, the operator will have to disengage the coronary artery, and reengage it with a better suited guide catheter that is stiffer and/or larger in diameter. This forces the operator to withdraw the coronary guide wire from its position beyond the stenosis tackled, a risky gamble since it may be difficult to cross the stenosis a second time owing to dynamic changes due to the preceding manipulations. Whichever one of these various strategies the operator chooses to pursue, they all involve additional time, radiation exposure to patient and personnel, and costly medical equipment while in no way guaranteeing success. In fact, not infrequently serious complications occur due to accidental total closure of an artery, coronary dissection, or patient exposure to excessive amounts of contrast material.

In addition to the publication of countless technical strategies for this common problem, numerous proposals for novel guide catheters have been made over the last three decades to eliminate guide support problems. While many of these equipment related proposals, a sampling of which is rendered below, display much ingenuity and creative thinking, their unifying feature seems to be that they are impractical or do not work, as evidenced by the fact that none of them is commonly used in clinical practice. In conclusion, there continues to be a need for a solution to the commonly encountered and dangerous 'lack of guide support' problem, a solution which is simple, practical, cost effective, and universally applicable.

The following possibly relevant U.S. Patents are incorporated herein by reference and listed chronologically. The order of listing is of no significance.

| Pat. No. | Title | Issue Date |
| --- | --- | --- |
| 4,748,982 | Reinforced Balloon Dilation Catheter with Slitted Exchange Sleeve and Method | Jun. 7, 1988 |
| 4,781,682 | Catheter Having Support Flaps and Method of Inserting Catheter | Nov. 1, 1988 |
| 4,813,930 | Angioplasty Guiding Catheters and Methods for Performing Angioplasty | Mar. 21, 1989 |
| 5,098,412 | Support System for Catheter | Mar. 24, 1992 |
| 5,263,963 | Expandable Cage Catheter For Repairing a Damaged Blood Vessel | Nov. 23, 1993 |
| 5,306,261 | Catheter with Collapsible Wire Guide | Apr. 26, 1994 |
| 5,336,184 | Rapid Exchange Catheter | Aug. 9, 1994 |
| 5,365,943 | Anatomically Matched Steerable PTCA Guidewire | Nov. 22, 1994 |
| 5,443,456 | Catheter with Collapsible Wire Guide | Aug. 22, 1995 |
| 5,456,667 | Temporary Stenting Catheter With One-Piece Expandable Segment | Oct. 10, 1995 |
| 5,681,280 | Catheter Control System | Oct. 28, 1997 |
| 5,733,248 | Universal Guide Catheter | Mar. 31, 1998 |
| 5,776,096 | Dual Lumen Vascular Catheter With Expanding Side Portal | Jul. 7, 1998 |
| 5,820,592 | Angiographic and/or Guide Catheter | Oct. 13, 1998 |
| 5,885,259 | Increasing Radius Curve Catheter | Mar. 23, 1999 |
| 5,941,872 | Method of Using an Increasing Radius Curve Catheter | Aug. 24, 1999 |
| 5,984,878 | Multi-Coating Stainless Steel Guidewire | Nov. 16, 1999 |
| 6,083,213 | Angioplasty Guide Catheter | Jul. 4, 2000 |
| 6,350,252 | Methods and Devices For Occluding The Ascending Aorta and Maintaining Circulation of Oxygenated Blood in the Patient when the Patient's Heart is Arrested | Feb. 26, 2002 |
| 6,595,952 | Guide Catheter with Backup Support System | Jul. 22, 2003 |
| 6,645,160 | Guide Support Catheter | Nov. 11, 2003 |
| 6,860,876 | Versatile Interventional Coronary Guiding Catheter | Mar. 1, 2005 |
| 7,497,853 | Deflectable Catheter Steering and Locking | Mar. 3, 2009 |

-continued

| Pat. No. | Title | Issue Date |
|---|---|---|
| 7,717,899 | Inner and Outer Telescoping Catheter Delivery System | May 18, 2010 |
| 7,993,303 | Stiffening Support Catheter and Methods for Using the Same | Aug. 9, 2011 |

BRIEF SUMMARY OF THE INVENTION

Designing guide catheters that are easy to handle and operate implies making the catheter slicker and thinner. Designing guide catheters that provide optimal support implies making the catheter thicker and bulkier. The fact that the functional goals of easy operation and good support can only be met with attempts to apply conflicting design strategies (i.e. increasing and decreasing catheter bulk at the same time) may well explain while all attempts to solve the 'lack of guide support' problem with changes to the instrument of operation itself appear to have failed.

The current invention takes a different approach. The present invention provides three embodiments. One of their unifying features is that they resolve the guide support issue using a second and separate support catheter, operated independently from the guide catheter. This support catheter is advanced with its distal end to a position adjacent to the distal end of the guide catheter. The distal end of the support catheter features a plurality of wire loops which can reversibly secure the distal end of the guide catheter on one side, while reversibly attaching themselves to the wall of the aorta on the opposing side.

The first embodiment provides a support catheter/support wire assembly, whereby manipulation of the support wires at the proximal end of the assembly changes leads to the reversible protrusion of wire loops from the catheter at the distal end of the assembly. Support to the guide catheter is provided by advancing the distal segment of the support catheter/support wire assembly to a position adjacent to the distal end of the guide catheter, adjusting the size and direction of the support wire loops, and engaging the distal end of the guide catheter.

The second embodiment provides a support wire assembly which can be used with any suitably shaped vascular catheter (e.g. a multipurpose shape), used as delivery catheter. The wire assembly consists of a single wire segment along its body, which, at its distal end, leads into a plurality of preformed elastic wire loops. Said elastic wire loops can be advanced out of, and retracted back into the delivery catheter. Owing to the inherent memory of the distal end of the wire assembly, its elastic loop shape will be immediately assumed when unconstrained. The loop segment can now be advanced to a position adjacent to the distal end of the guide catheter to provide support.

The third embodiment provides a wire-catheter assembly with a multiple elastic wire elements at the end thereof. Pulling on an actuator running along the lumen of the catheter leads to a conformational change of these wire elements from a straight to an extended, curved or looped shape. Using methods similar to those employed by the first two embodiments, the wire-catheter assembly can be brought adjacent to the distal end of a guide catheter to stabilize its position during a coronary intervention.

The present invention offers reliable guide support, since the wire loops in all three embodiments will prevent dislodgement of the guide in all possible directions including lateral, anterior, and posterior.

Manipulation of the guide catheter is easier and more precise, since its task is now limited to delivering the equipment into the coronary, rather than providing delivery and support at once.

There is no need to exchange guide wires, there is no need for additional guide wires or buddy wires. There is no need for catheter exchanges, and, consequently, there is a significantly reduced chance of losing access across the lesion, significantly reducing the risk of the procedure.

The invention is primarily intended for use on a standby basis, offering reliable guide support should the need arise. The operator will therefore be able to choose 'non-aggressive' guide shapes and will not have to resort to aggressive guide engagement tactics such as 'deep-throating', again decreasing the risk of the procedure. The only added step needed with this invention is the placement of a second vascular access, with minimal risk.

Anticipating guide support problems due to difficult lesions or anatomic situations, the operator may opt to use the present invention from the outset of the procedure. In this case, there is a reduced need for preliminary manipulations such as pre-dilatations. Primary stenting is significantly facilitated.

Difficult coronary interventions can be done quicker, more safely, and more successfully.

Reduced complication rates, waste of equipment and time will lead to significant cost savings.

The present invention provides a guide catheter apparatus that includes a first catheter body having a proximal end, a distal end, at least one inner lumen, and an outer surface. A plurality of support members are attached to the outer surface of the catheter body at the distal end thereof. The support members are movable between a resting configuration and a support configuration wherein the support members can be curved, and each extending away from said outer surface into different directions. The catheter body has recesses at its distal end, the recesses receiving the support members in their resting position.

A second catheter body is a guide catheter. The support members provide support to the first catheter outer surface, wherein two of the support members create the first catheter body outer surface when in the support configuration.

In one embodiment, one or more support members are slidably attached to the first catheter body apparatus and wherein movements of the support members towards the distal end of said catheter body enable a flexing away of each support member from the distal end of said catheter, and movement of said support member towards the proximal end of said catheter positions the support member adjacent to said catheter.

In one embodiment, one or more of the flexible support members are wires.

In one embodiment, one or more wires run from the distal end towards the proximal end of the catheter body and through one or more elongated tubular openings within the catheter body.

In one embodiment, each of said one or more elongated tubular openings can be reversibly opened or closed at the proximal end of the catheter, allowing each of the tubular openings to be flushed and aspirated.

In one embodiment, the wires can be locked in a selected position with one or more hemostatic O-rings located at the proximal end of said catheter.

In one embodiment, a catheter apparatus includes a catheter body having a proximal end, a distal end, at least one inner lumen, and an outer surface with a diameter of 6 F or less.

In one embodiment, a plurality of flexible support members are attached to the outer surface of said catheter body at the distal end thereof.

The support members are movable between a first resting configuration positioned, and a support configuration wherein the support members can be smoothly curved and extending away from the catheter body outer surface.

A second catheter body is a guide catheter, the supporting members providing support to the first catheter outer surface, wherein two of the support members create the first catheter body outer surface when in the support configuration.

In one embodiment, one or more support members run slidably from their distal attachment at said catheter body to the proximal end of the catheter body, whereby movements of the support members towards the distal end of the catheter body lead to the flexing away of support means from a defined section near the distal end of the catheter (hereafter referred to as the support section), and movement of the support means towards the proximal end of said catheter lead to their positioning adjacent to said catheter.

In one embodiment, one or more of the flexible support members are wires.

In one embodiment, one or more wires run from the distal support section towards the proximal end of the catheter through elongated tubular openings within the catheter body.

In one embodiment, each of the elongated tubular openings connects can be reversibly opened or closed at the proximal end of the catheter, allowing each of the tubular openings to be flushed and aspirated.

In one embodiment, the wires can be reversibly locked in their positions by way of hemostatic O-rings at the proximal end of said catheter.

A first embodiment of this invention provides a support catheter member assembly, to be used preferably for cardiac interventional procedures, comprising an elongated tubular body having a proximal and a distal end, and a plurality of lumina extending axially therethrough. A plurality of support members (e.g. wires) extend through the catheter, exit the catheter at a defined distance from its distal opening, and reattach to the catheter at its distal end. Manipulation of these support members leads to their flexing outward or to their retraction towards the catheter, thereby providing an adjustable support assembly with which the position of a separate coronary guide catheter can be stabilized. In a second embodiment, a support catheter member assembly comprising wires is presented which has a pre-shaped, flexible distal configuration. The wire assembly can be delivered through vascular catheters. The wire assembly assumes its pre-shaped distal configuration as soon as it exits the catheter. The wire assembly can be used to stabilize the position of a separate vascular guide catheter. A third embodiment provides a support catheter member assembly including wires. Wires are firmly attached with one end to a distal point of the catheter, and firmly attached with their opposing ends to an actuator member which is running through the catheter bore exiting at its proximal end. Moving the actuator allows the operator to bend the support wire assembly towards an outwardly flexed conformation. The support catheter member assembly including wires is then suited to stabilize the position of a separate vascular guide catheter.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 8 is a side view of a preferred embodiment of the apparatus of the present invention;

FIG. 9 is a schematic diagram showing sectional views of a preferred embodiment of the apparatus of the present invention, each section being a sectional view taken from FIG. 8, each section view of FIG. 9 being designated by the numeral 9 followed by the letters a, b, c, d, e, for g;

FIG. 11 is indicated by a dotted line of each of the four corresponding horizontal or transverse cross sectional views, and wherein correlation of the cross sectional views with corresponding positions indicated by lower case letters "e, d, c, g";

FIGS. 12, 13, 14 depict various views of a second embodiment of the present invention, wherein FIG. 12 is a perspective view of the distal end of the delivery catheter/support wire assembly in its operational position, FIG. 13 is a fragmentary schematic view of the distal end of the delivery catheter/support wire assembly in a retracted position, and FIG. 14 is a perspective view of a loading tool used to facilitate introduction of the support wire assembly into the delivery catheter;

FIG. 19 is a side view of a third embodiment of the apparatus of the present invention;

FIGS. 20 and 21 are partial perspective views of the distal end of the third embodiment with the support elements in their extended (FIG. 20) and retracted (FIG. 21) positions;

FIG. 22 shows two horizontal plane cross sectional views of the third embodiment, with lower case letters indicating their location in relation to the side view offered in FIG. 23; and FIG. 23 offers a partial perspective view a section of the third embodiment close to the distal end thereof.

DETAILED DESCRIPTION OF THE INVENTION

Figure 1:
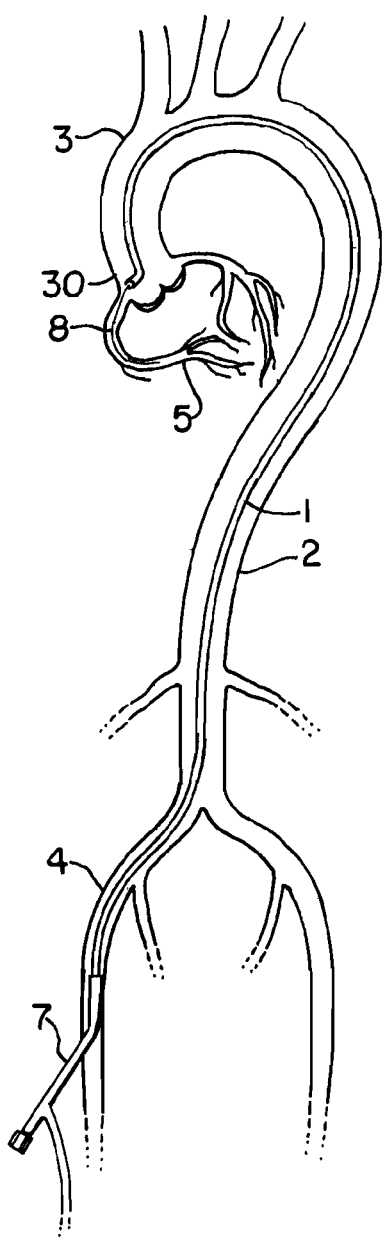
FIG. 1 is a schematic view of a typical coronary intervention, with a catheter entering the vascular system at the level of the femoral artery, traversing the aorta, and engaging a coronary artery.
Figure 2:
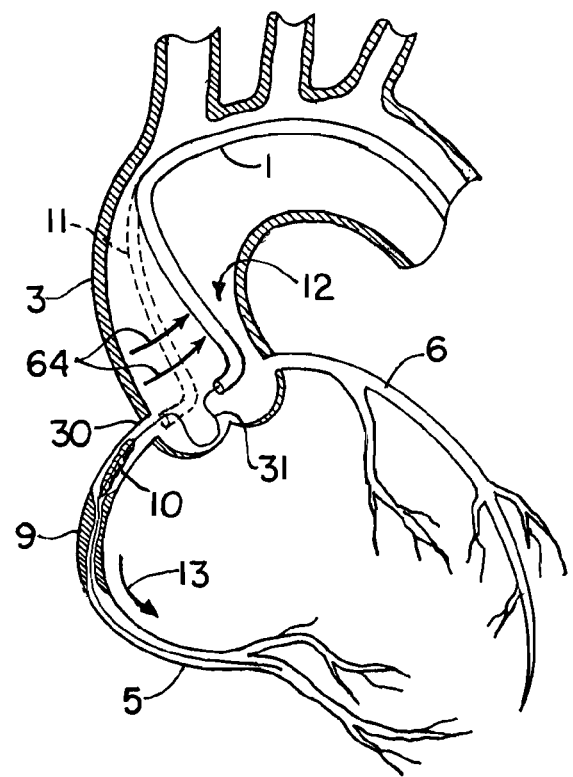
FIG. 2 is a schematic view of the aortic arch, the coronary vessels, a guide catheter, and a balloon catheter and wire assembly, illustrating the problem to be resolved with the present invention.
Figures 3, 4:
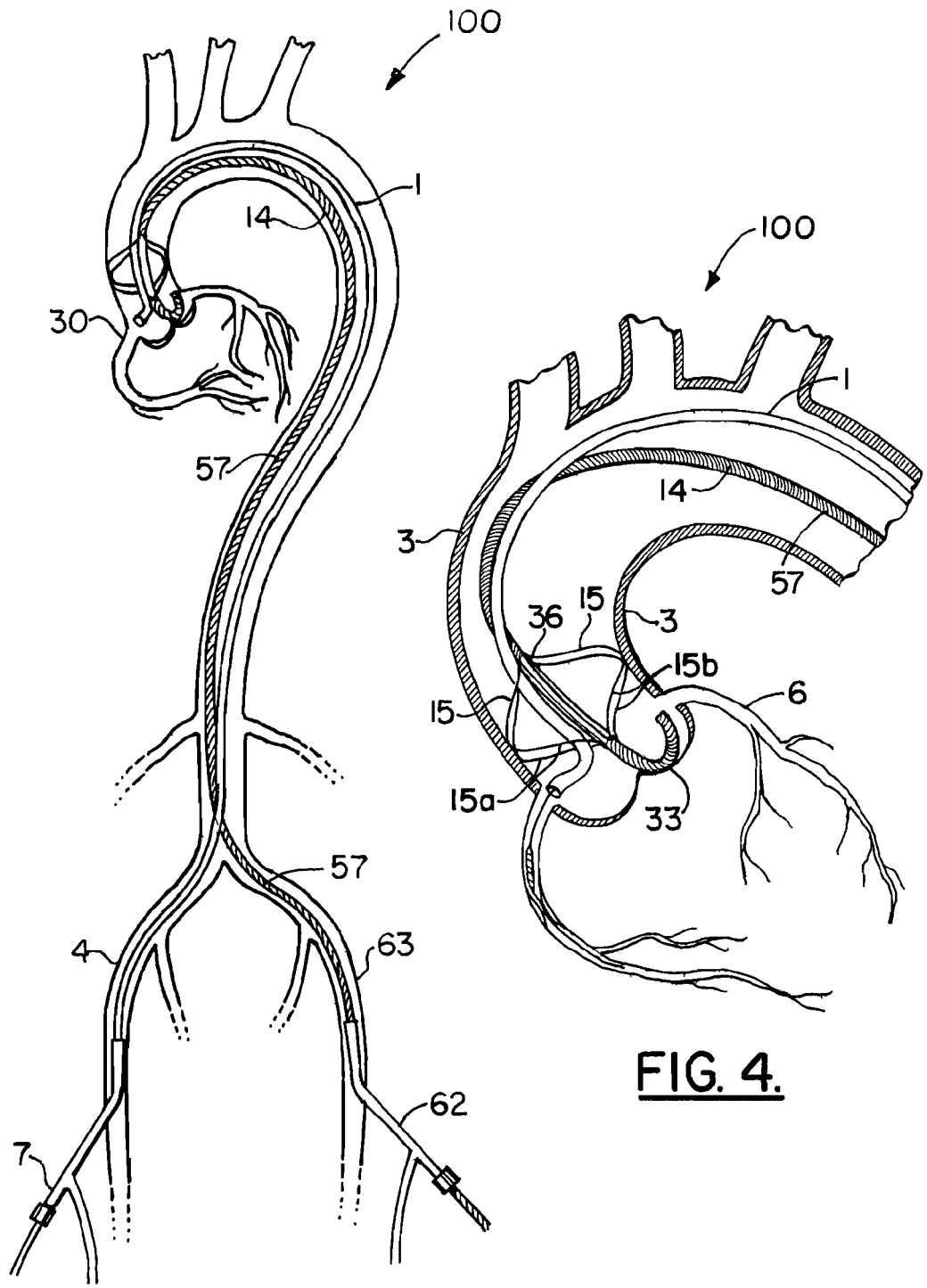
FIG. 3 is a schematic view of a preferred embodiment of the apparatus of the present invention, showing an entry into the vascular system at the opposing femoral artery.
FIG. 4 is a schematic enlarged view of a preferred embodiment of the apparatus of the present invention.

FIGS. 1-4 show generally a preferred embodiment of the apparatus of the present invention, designated generally by the numeral 100 in FIGS. 3-4. In FIG. 1, the first step of the method of the present invention employs guide catheter 1 which enters the vascular system through an access sheath 7 (commercially available) in the femoral artery 4, traverses the abdominal aorta 2 and ascending aorta 3 and engages the right coronary ostium 30 of the right coronary artery 5, into which a coronary wire 8 is introduced.

FIG. 2 further illustrates the method and apparatus of the present invention. Depicted are the ascending aorta 3, the right coronary artery 5, and the left coronary system 6. Guide catheter 1 has been advanced with its tip into right coronary ostium 30, coronary wire 8 has been steered through stenosis 9 into the distal portions of right coronary artery 5, and attempts are in progress to advance undeployed stent 10 through stenosis 9 in the direction of arrow 13 in FIG. 2. Owing to resistance offered by stenosis 9, coronary wire 8 can buckle at 31, wherein guide catheter 1 is pushed away from right coronary ostium 30 (see arrows 64, FIG. 2), moving it from engaged position 11 (phantom lines) towards dislodged position 12 in FIG. 2.

FIG. 3 further shows the method and apparatus of the present invention, the vascular system corresponding to FIG. 1, with the first catheter and second catheter 57 in place. Guide catheter 1 enters the vascular system through access sheath 7 at the femoral artery 4, and has been advanced with its tip engaged in coronary ostium 30. Support catheter 14 enters through a second access sheath 62 at opposing femoral artery 63, and has been advanced with its pigtail shaped tip 33 (see FIG. 4) to a position adjacent to the tip of guide catheter 1.

FIG. 4 illustrates further the method and apparatus of the present invention. In FIG. 4, distal split support wires 36 form a plurality of loops 15 exiting from support catheter 14. In FIG. 4, loops 15 have engaged and support guide catheter 1. There can be for example, four (4) radially extending loops 15, each loop being circumferentially spaced from another loop (e.g., ninety degrees apart). In FIG. 4, two of the loops 15a engage guide catheter 1, one loop 15a on one side of guide catheter 1 and another loop 15a on the other side of guide catheter 1. Each loop 15a can also engage the aorta 3 just above ostium 30 as shown in FIG. 4. At the side opposite to this engagement of loops 15a against guide catheter 1 and aorta 3, support wire loops 15b (e.g., two (2) loops 15b) abut against ascending aorta 3, thereby securing the position of guide catheter 1. This arrangement prevents any dislodgement of catheter 1 from its engagement in coronary ostium 30.

Figure 5:
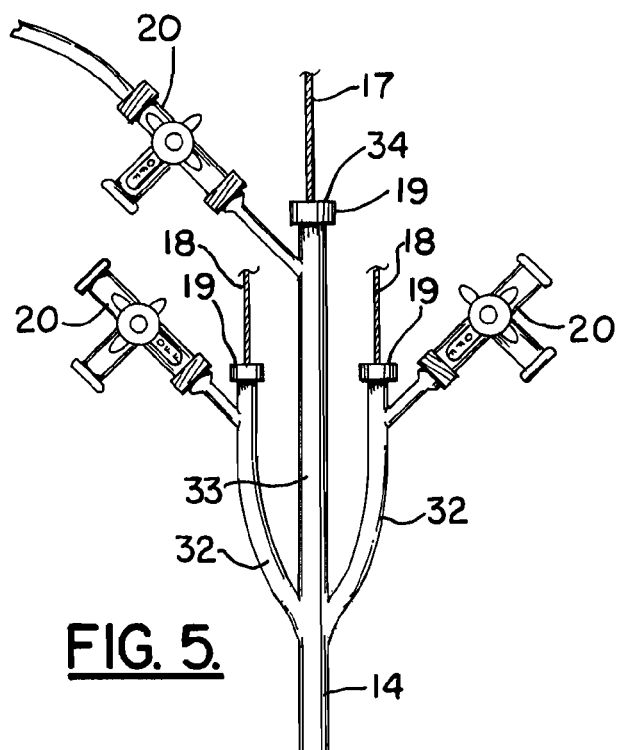
FIG. 5 is a fragmentary view of a preferred embodiment of the apparatus of the present invention.
Figure 6:
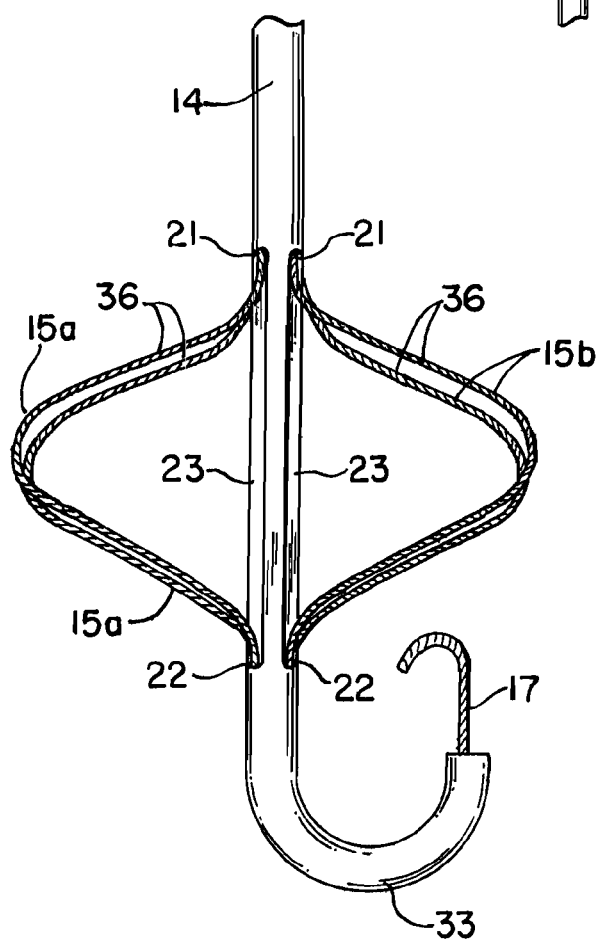
FIG. 6 is a fragmentary side view of a first embodiment of the apparatus of the present invention.
Figure 7:
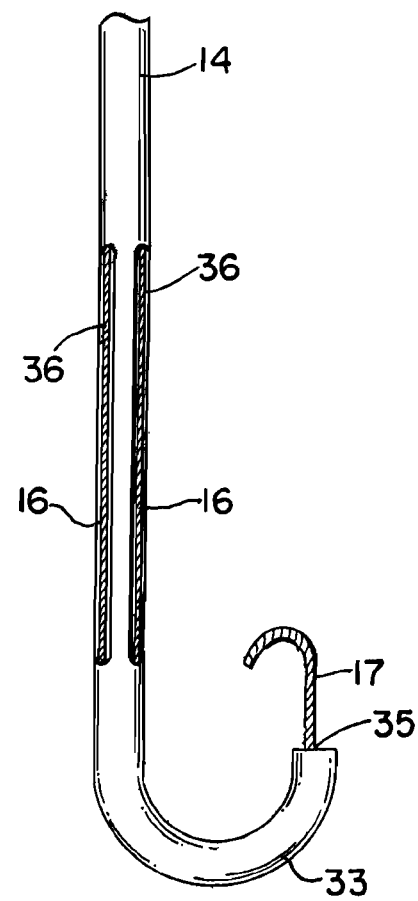
FIG. 7 is a side view of the first embodiment of the apparatus of the present invention.

FIGS. 5-7 show the structure of support catheter 14 in more detail. FIG. 5 illustrates the proximal end of support catheter 14, splitting into two support wire endings 32 and a single J-wire ending 33. Proximal support wires 18 and J-tipped wire 17 exit the catheter through hemostatic O-rings 19. Support wire endings 32 and J-wire ending 33 feature commercially available 3-way stopcocks 20, to allow for all wire bearing parts of support catheter 14 to be properly flushed and aspirated.

FIG. 6 shows the distal end of support catheter 14, with distal split support wires 36 forming loops 15 exiting catheter 14 at exit openings 21 and reentering catheter 14 at entry openings 22. Shown are also longitudinal support wire recesses 23. J-tipped wire 17 exits catheter 14 at its distal most portion as shown.

FIG. 7 shows the distal end of support catheter 14, with distal split support wires 36 now in their retracted position which is designated by the numeral 16, fitting snugly into support wire recesses 23. Viewing FIGS. 5-7 in their ensemble, the function of support catheter 14 becomes readily apparent. Proximal support wires 18 are advanced into support catheter 14. Distal split support wires 36, as depicted in FIG. 7 in their retracted position 16, are firmly attached with their distal ends at entry points or openings 22 and cannot advance coaxially with the catheter. Therefore, any forward movement of proximal joined support wires 18 leads distal split support wires 36 to assume the formation of loops 15. The position of proximal joined support wires 18 in relation to support catheter 14 can be secured with hemostatic O-rings 19, allowing an operator to form the distal support wires 36 into loops 15 of the exact size needed in any particular anatomic situation. Note that, within support catheter 14 each proximal support wire 18 splits into two distal support wires 36, as further illustrated in subsequent figures. Note further that FIGS. 5-7 also depict J-tipped wire 17, both at its proximal 34 and distal 35 exit points. J-tipped wire 17 is a standard feature of any vascular catheter, used to deliver the catheter into its intended position and thereafter removed. J-tipped wire 17 does not have any particular role or function in the current invention beyond its use for catheter delivery, and has been depicted here for better clarity only.

FIG. 8 represents a side view of support catheter 14, with various locations of sectional views 9a, 9b, 9c, 9d, 9e, 9f, 9g indicated on FIG. 8. For example, FIG. 8 provides sections at "a" and "g", marked 9a, 9g. In FIG. 9, these sectional views are "a", "g" and are the same configuration. FIG. 9b is a section at 9b of FIG. 8. FIG. 9b shows wires 36 in expanded position to form loops 15a, 15b. FIG. 9c shows wires 36 in the collapsed position 16. FIG. 9 thus presents a series of transverse or horizontal cross sectional views of catheter 14 corresponding to these various locations 9a-9g of FIG. 8.

As can be seen, the number of lumina within the catheter changes from proximal (bottom of FIG. 8) to distal (top of FIG. 8). Proximal joined support wires 18 and J-wire 17 have one lumen each, as exemplified by locations 9f and 9g in FIG. 8 and corresponding figures. At its proximal and mid sections, as exemplified by location 9e of FIG. 8, support catheter 14 has three lumina, two proximal support wire lumina 26 and central catheter lumen 24. Further distally, as exemplified by location 9d, proximal support wire lumina 26 have each split into two distal split support wire lumina 25, central catheter lumen 24 remains unchanged for all locations. Locations 9c and 9b are identical, whereby cross sectional view 9b depicts the catheter 14 with distal split support wires 36 in their extended position 15, leaving support wire recesses 23 empty, and cross sectional view 9c depicts the catheter with its distal split support wires 36 in their retracted position 16, now filling recesses 23.

Figure 10:
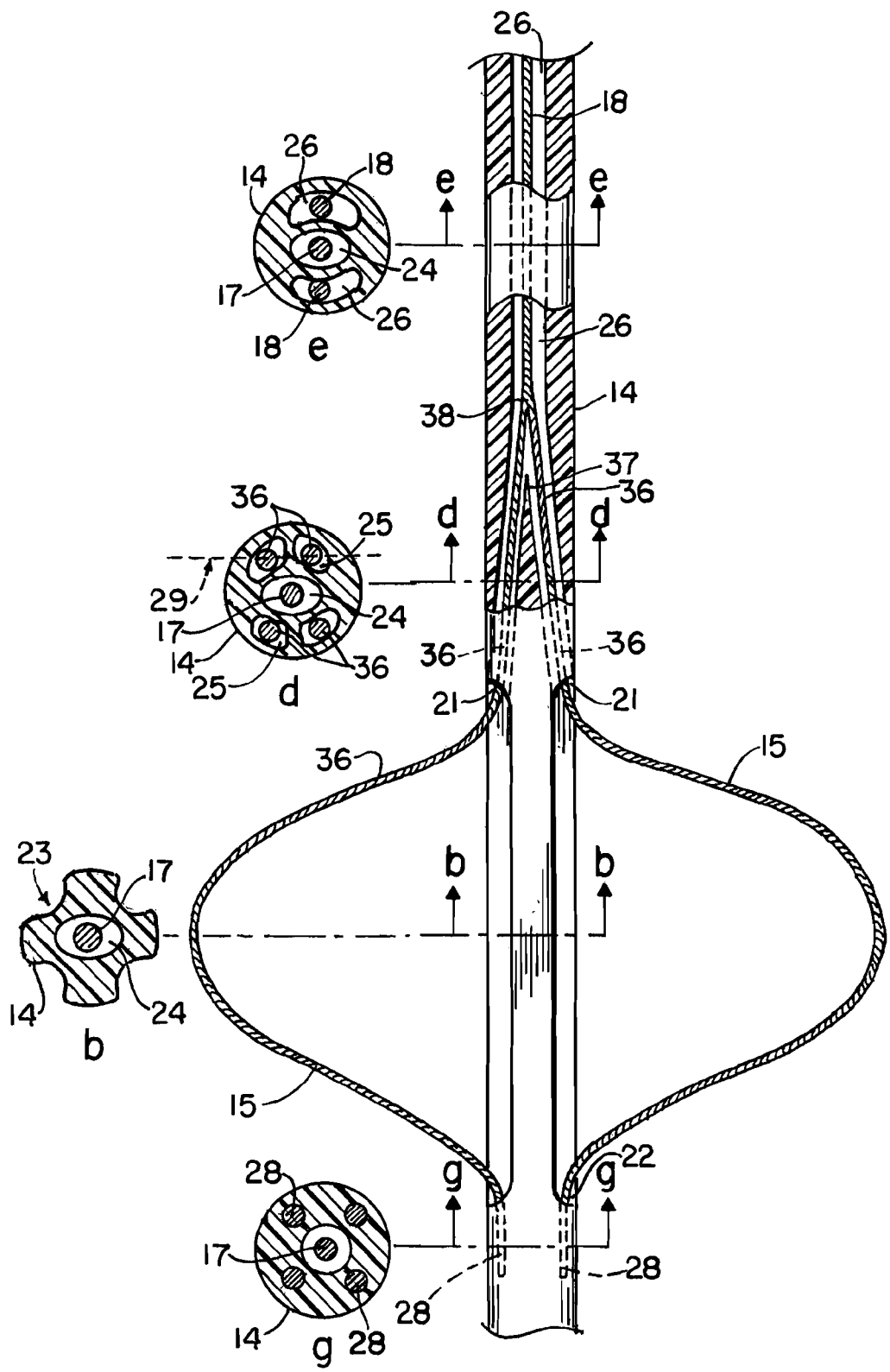
FIG. 10 is a frontal cross sectional view of a preferred embodiment of the apparatus of the present invention illustrating a distally located segment of the first embodiment of the present invention, with support wires in the operational position, and with adjacent four corresponding horizontal cross sectional views of the catheter, with the position of each cross sectional view indicated by arrows, and wherein their positions in relation to FIG. 10 is indicated, following the lower case labeling of FIG. 10.

FIG. 10 is a frontal plane cross sectional view of a distal portion of support catheter 14. Corresponding horizontal cross sectional views are displayed at various points e, d, b, g. The location of the horizontal cross sectional views in relation to the frontal plane cross sectional view is indicated by lower case letter labeling, and follows the pattern established in FIGS. 5-7. Further, the location of the frontal plane cross sectional view in relation to the horizontal cross sectional views is given by broken plane marker line or reference line 29. Proximal joined support wire 18 is located in proximal support wire lumen 26, with support wire split point 38 right above lumen split point 37 and proximal joined support wire 18 in a position of maximal forward extension, limiting the potential size of distal split support wire loops 15.

Figure 11:
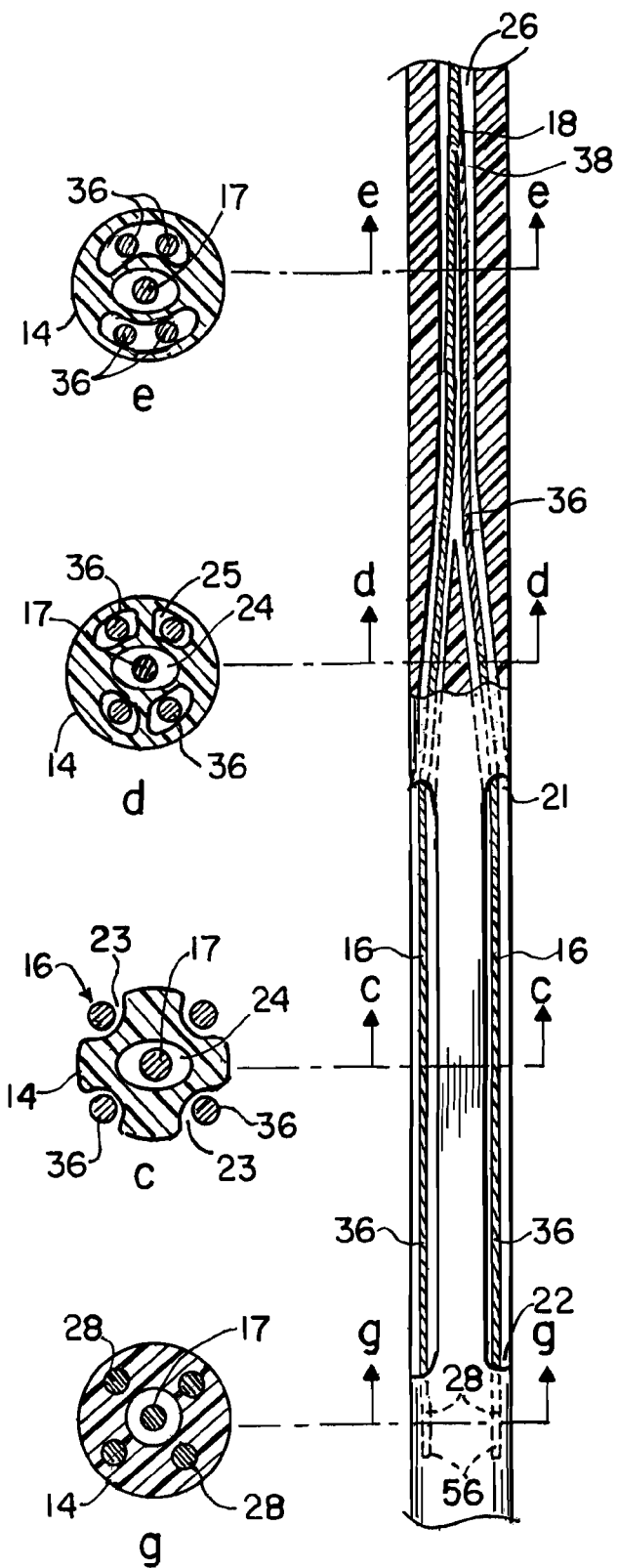
FIG. 11 is a frontal cross sectional view of a preferred embodiment of the apparatus of the present invention showing a distally located segment of the first embodiment of the present invention, with the support wires in the retracted position, adjacent four horizontal cross sectional views of the catheter, with the position of each cross sectional view indicated by arrows, and wherein the plane of frontal cross sectional

FIG. 11 shows the same distal portion of support catheter 14 displayed in FIG. 5, with the same combination of frontal plane and horizontal plane cross sectional views. FIG. 11, however, shows distal split support wires 36 in their retracted position 16 within support wire recesses 23. Proximal joined support wire 18 has been retracted maximally, with support wire split point 38 and lumen split point 37 at their maximal distance of separation. Note that anchored support wire ends 28 are firmly embedded in support catheter wall bulge or outpouch 56, which limits the degree to which proximal support wire 18 can be retracted.

Figure 12:
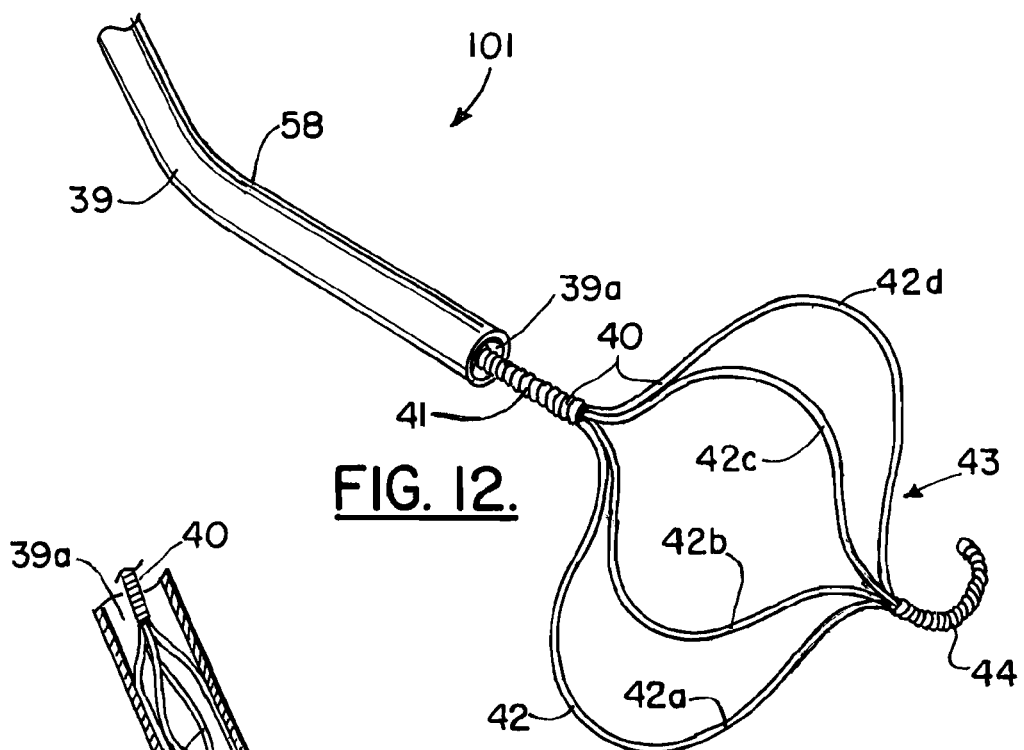

FIG. 12 show a second embodiment of the present invention designated generally by the numeral 101. In FIG. 12, there is a vascular catheter hereafter referred to as second delivery catheter 58 having catheter body 39 with lumen 39a. While many readily available catheter shapes would seem suitable, a standard multipurpose catheter shape is depicted. Unified support wire 40 consists of a long proximal joined portion 41, pre-shaped split wire portion 42 which includes multiple wires 42a-42d, and J-shaped distal joined portion 44.

Figure 13:
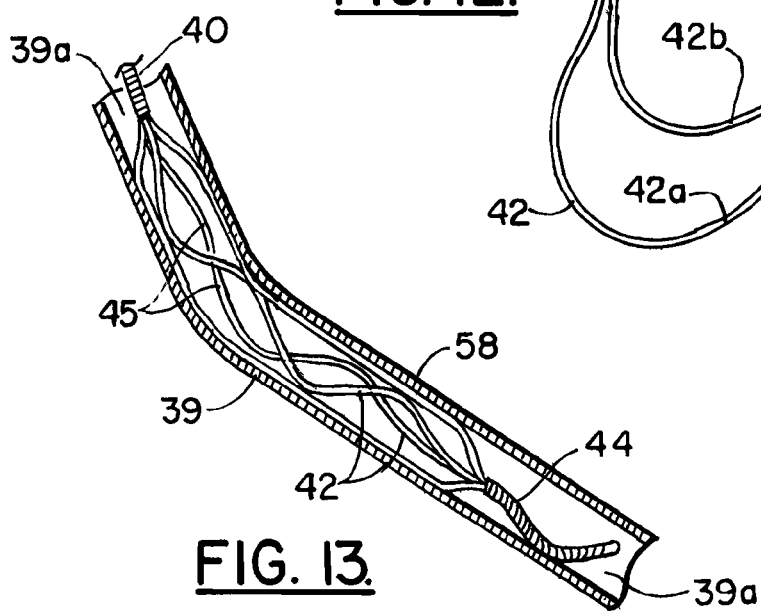

FIG. 13 depicts the distal segments of catheter body 39 having lumen 39a and unified support wire 40. As can be seen, proximal joined wire portion 41 splits into pre-shaped split wire portion 42 which, following inherent memory, assumes loop configuration 43 and, at its distal end, recombines to form distal joined wire portion 44. Retraction of unified support wire 40 into catheter body 39, as depicted in FIG. 13, makes pre-shaped split wire portion 42 adapt to the lumen size of catheter body 39, thereby losing loop configuration 43 and assuming the compressed shape that is designated as 45 in FIG. 13.

Figure 14:
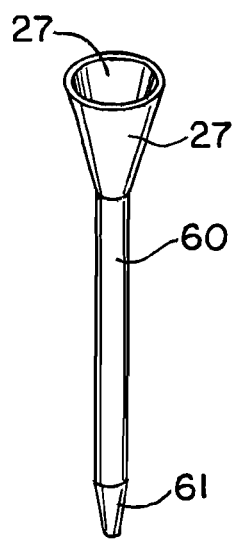

This second embodiment 101 of the present invention is delivered by first advancing delivery catheter 58 having catheter body 39 into position with the assistance of a standard J-tipped wire 17. J-tipped wire 17 is then withdrawn, and unified support wire 40 is introduced into catheter body 39 with the aid of loading tool 60 (FIG. 14). Loading tool 60 can be a simple tubular structure with a pointed distal tip 61 and a funnel shaped entry 27. Unified support wire 40 is back loaded into funnel shaped entry 27 of loading tool 60 which, with its pointed tip 61, is now used to introduce the tip of unified support wire 40 into the proximal end of catheter body 39. Loading tool 60 can be withdrawn as soon as all of pre-shaped split wire portion 42 is inside catheter body 39. A hemostatic device such as O-ring 19 is then back-loaded onto unified support wire 40 and catheter body 39, and the tip of unified support wire 40 can then be advanced to the distal end of catheter body 39.

Figure 15:
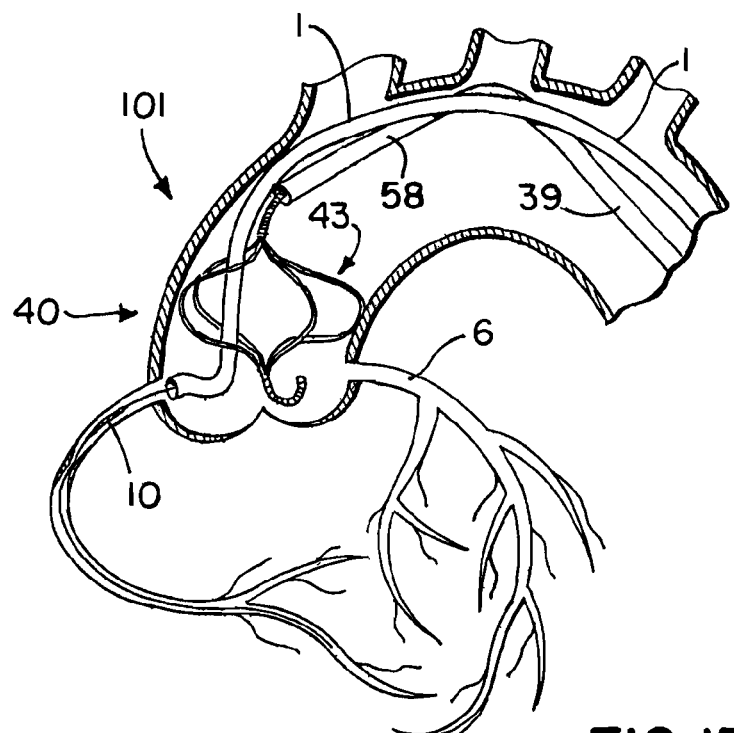
FIG. 15 is a schematic view of the second embodiment of the apparatus of the present invention showing the ascending aorta and guide catheter/support wire interaction without the delivery catheter.

FIG. 15 shows the distal portion of unified support wire 40 securing the position of the distal portion of guide catheter 1, following basically the same method illustrated in FIGS. 1-4 with the first embodiment 100 of the present invention. As is readily apparent, retraction of unified support wire 40 into catheter body 39 allows to rapidly remove both of these instruments as soon as stent 10 has been delivered and support of guide catheter 1 is no longer needed.

Figure 16:
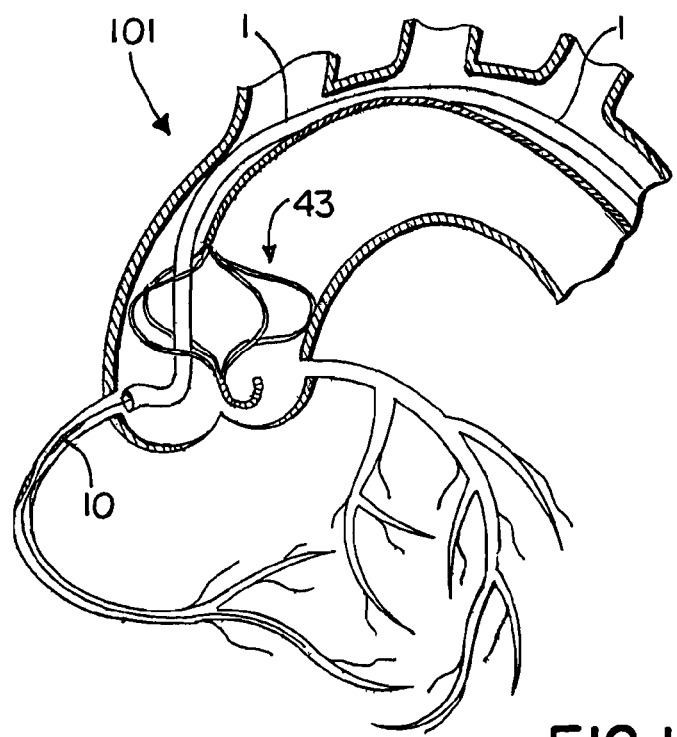
FIG. 16 is a schematic view of the second embodiment of the apparatus of the present invention showing the ascending aorta, guide catheter/support wire interaction with the delivery catheter in place.

FIG. 16 shows a special feature of this alternative embodiment 101. While unified support wire 40 will have to be delivered and removed with catheter body 39, continuous use of catheter body 39 is not needed once a secure support position adjacent to guide catheter 1 had been established. This allows to use catheter body 39 only for short periods of time, obviating the need for a second pressure line and manifold on the catheterization table. Should unified support wire 40 be intended for use without catheter body 39, it would have to be made in standard 'exchange length size'. Appropriate hydrophilic surface coating of all exposed portions of unified support wire 40, all blood exposed wire parts of the embodiments of this invention is needed.

Figures 17, 18:
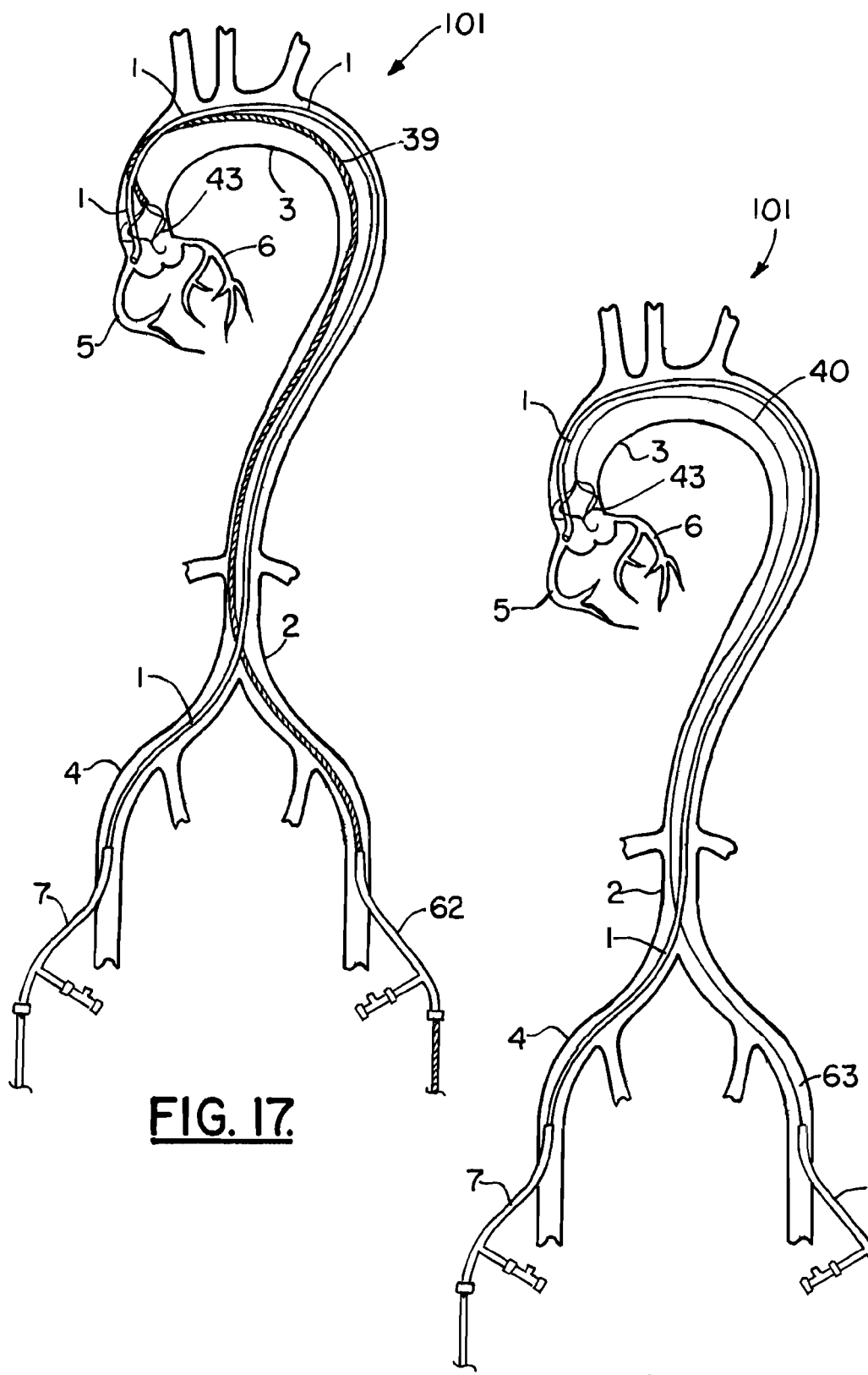
FIG. 17 is a schematic view of the second embodiment of the present invention, showing the interaction of a coronary guide catheter with the delivery catheter left in place.
FIG. 18 is a schematic view of the second embodiment of the present invention, showing the interaction of a coronary guide catheter wherein the delivery catheter has been removed.

FIGS. 17-18 present this second embodiment 101 of the present invention in an overview similar to the one provided in FIG. 2 for the first embodiment 100. FIG. 17 shows the loop configuration 43 of pre-shaped split wire portion of unified support wire 40 supporting guide catheter 1, with catheter body 39 in place. In FIG. 18 delivery catheter body 39 has been removed.

FIGS. 19-23 present a third embodiment 102 of the present invention. As with the first two embodiments, a wire loop configuration is used to entrap the guide catheter to be stabilized. FIG. 19 provides a side view of this embodiment 102, which consists of a catheter-wire assembly. Catheter 59 of this third embodiment 102 has a catheter body 46 with single lumen 54 which houses an actuator wire 49, running through said single lumen 54 from the proximal to the distal end of catheter body 46. A plurality of wire elements 47 are firmly anchored with their proximal ends 51 in the wall of catheter body 46 at anchor points 50. Distally, wire elements 47 join actuator wire 49 to form J-tipped joined wire ending 48. The proximal end of catheter 46 shows hemostatic O-ring 19 reversibly closing the single lumen 54 of catheter 46, while simultaneously locking actuator wire 49 in any chosen degree of wire extension. A catheter side port 55 and a three way stopcock 20 are provided to allow for single lumen 54 to be properly flushed and aspirated. FIG. 20 offers a view of the distal end of the third embodiment 102 showing wire elements 47 in their looped configuration 52. A backward pulling of actuator wire 49 towards the proximal end of catheter 46 leads wire elements 47 to form looped configuration 52. Forward pushing of actuator wire 49 leads wire elements 47 to assume their retracted position 53, adjacent and essentially parallel to actuator wire 49, as depicted in FIG. 21.

FIG. 22 shows two horizontal plane or transverse cross sectional views of this third embodiment 102, their location in relation to overview FIG. 22 is indicated by section lines 22a in FIG. 23 for section "a" in FIG. 22. FIG. 22 view "b" is a sectional view taken along lines 22b-22b of FIG. 23. Location a of FIG. 22 is situated at the proximal end of wire elements 47, which are shown firmly embedded in the wall 132 of catheter 46 at entry points 50. Shown are also single lumen 54 and catheter wall outpouches 56 which, at that particular location allow for the anchoring of wire elements 47. Location b of FIGS. 22-23 show the simplicity of the embodiment, with catheter wall 56 surrounding single lumen 54 which, in turn, houses actuator wire 49.

FIG. 23 illustrates the anchoring of the proximal ends of wire elements 47 into catheter wall 132, offering a partial perspective view. Unlike the first 100 and second 101 embodiments of this present invention, this third embodiment 102 can be safely advanced through the vascular system (when wire elements 47 are in their retracted position 53) without the rail support of a standard J-tipped wire 17.

The following is a list of parts and materials suitable for use in the present invention:

PARTS LIST

Part Number Description 1 guide catheter
2 abdominal aorta
3 ascending aorta
4 femoral artery
5 right coronary artery
6 left coronary artery
7 access sheath
8 coronary wire
9 stenosis
10 coronary stent
11 engaged catheter position
12 dislodged catheter position
13 arrow
14 support catheter
15 distal split support wire loops
15a distal split support wire loops
15b distal split support wire loops
16 distal split support wire, retracted position
17 J-tipped wire
18 proximal joined support wire
19 hemostat O-ring
20 3-way stopcock
21 support wire exit opening
22 support wire entry point/opening
23 support wire recess
24 central catheter lumen
25 distal split support wire lumen
26 proximal support wire lumen
27 funnel shaped entry of loading tool
28 anchored support wire ends
29 plane marker line
30 right coronary ostium
31 buckling coronary wire
32 support ending
33 pigtail ending of catheter/J-wire ending
34 proximal J-wire exit point
35 distal J-wire exit point
36 distal split support wires
37 lumen split point
38 support wire split point
39 catheter body
39a lumen
40 unified support wire
41 proximal joined wire portion of unified support wire
42 pre-shaped split wire portion
42a wire
42b wire
42c wire
42d wire
43 loop configuration of pre-shaped split wire portion
44 distal joined wire portion of unified support wire
45 compressed shape of pre-shaped split wire portion
46 catheter body
47 wire elements of third embodiment
48 J-tipped joint wire ending
49 central actuator wire
50 anchor entry points of wire elements of third embodiment
51 proximal end wire elements of third embodiment
52 looped configuration
53 retracted configuration
54 single lumen of catheter of third embodiment
55 catheter side port
56 catheter wall outpouch/bulge/thickened section
57 second catheter
58 second catheter
59 second catheter
60 loading tool
61 pointed tip of loading tool
62 second access sheath
63 opposing femoral artery
64 arrow
100 guide catheter support apparatus
101 guide catheter support apparatus
102 guide catheter support apparatus
132 wall of catheter of third embodiment All measurements disclosed herein are at standard temperature and pressure, at sea level on Earth, unless indicated otherwise. All materials used or intended to be used in a human being are biocompatible, unless indicated otherwise.

The invention claimed is:

1. A support catheter apparatus of an outer diameter of 6 F or less, to be used to provide positional support within an ascending aorta for a separate medical instrument used during a coronary interventional procedure, the support catheter apparatus comprising:
 (a) a catheter body having a proximal end, a distal end, a longitudinal axis, one or more elongated, tubular inner lumina, and an outer surface;
 (b) the catheter body being sufficiently flexible to bend at 180°, allowing for its positioning around an aortic arch;
 (c) one or more support members forming a support section at the distal end of the catheter body, whereby, in the support section, the one or more support members, each having a distal end, are configured to shift between a resting configuration, wherein the one or more support members are positioned generally adjacent to the outer surface of the catheter body, and a support configuration, wherein the one or more support members assume a curved or loop shape extending away from the outer surface of the catheter body;
 (d) wherein each distal end of the one or more support members attach to the catheter body at or near the distal end of the catheter body;
 (e) wherein the one or more support members, attached at or near the distal end of the catheter body, are located outside of the catheter body;

(f) wherein the one or more support members, proximal to the support section, enter into the one or more elongated, tubular inner lumina inside the catheter body at one or more distal luminal exit points and exit the catheter body at one or more proximal luminal exit points;

(g) wherein one or more stopcocks connect to the one or more proximal luminal exit points, thereby enabling aspiration and flushing of the one or more elongated, tubular inner lumina;

(h) wherein by advancing the one or more support members into the one or more proximal luminal exit points, said one or more support members, upon exiting the one or more distal luminal exit points, assume the support configuration;

(i) wherein, by retracting the one or more support members at the one or more proximal luminal exit points out of the catheter body, said one or more support members enter into said one or more distal luminal exit points and assume the resting configuration; and (j) whereby the one or more support members have a hydrophilic surface and are made entirely or in part of metal or metal alloy.

2. The support catheter apparatus of claim 1, wherein the distal end of the catheter body has a pigtail shaped tip.

3. The support catheter apparatus of claim 1, wherein the one or more support members comprises at least two support members, and wherein the at least two support members are positioned at opposing sides in relation to the longitudinal axis of the catheter body along the support section.

4. The support catheter of claim 1, whereby the catheter body, at or near its proximal end, furcates into a plurality of individual catheter ends, whereby each of the elongated, tubular inner lumina of the catheter body leads into a respective one of the plurality of individual catheter ends and exits the catheter body at the proximal end of the catheter body.

5. The support catheter of claim 1, wherein the one or more support members comprises at least two support members, and wherein the at least two support members enter the catheter body through at least two of the one or more elongated, tubular inner lumina proximal to the support section, and wherein the at least two support members of the plurality of support members within the at least two elongated, tubular inner lumina join within the catheter body, forming a combined lumen and a combined support member.

6. The support catheter of claim 5, wherein the combined lumen and the combined support member exit the catheter body at the proximal end.

7. The catheter of claim 5, wherein the combined lumen comprises a plurality of combined lumen and the combined support member comprises a plurality of combined support members exiting the catheter body at its proximal end.

8. The support catheter apparatus of claim 1, further comprising:

(k) the one or more support members at the support section of the catheter body comprising a plurality of support members including a first group of support members and a second group of support members;

(l) wherein the first group of support members, when in the support configuration, is configured to engage an endovascular surface;

(m) wherein the second group of support members, when in the support configuration, is configured to engage and positionally support a separate medical instrument located outside of the catheter body simultaneously to the first group engaging the endovascular surface; and (n) wherein the engagement of the endovascular surface and the separate medical instrument positions the distal end of the catheter body between the engaged endovascular surface and a distal end of the engaged separate medical instrument.

9. The support catheter apparatus of claim 1, further comprising:

(k) an actuator section formed by the one or more support members exiting the catheter body at or near the proximal end of the catheter body at the one or more proximal luminal exit points enabling the one or more support members to advance into or retract from the catheter body;

(l) at least one hemostatic O-ring attached to the one or more proximal luminal exit points that enable an operator to positionally secure the one or more support members.

10. The support catheter apparatus of claim 1, (k) wherein, a first group of two of the one or more support members, when in their support configuration, extend away from the longitudinal axis of the catheter body by an angle relative to each other that is less than 180°;

(l) wherein, owing to: (i) the attachment of the catheter body to the distal ends of the one or more support members, (ii) the entering of the one or more support members into the one or more elongated, tubular inner lumina inside the catheter body, and (iii) the one or more support members having the hydrophilic surface and being made entirely or in part of metal or metal alloy, the first group of two support members, when exposed to external forces, radially extend from the catheter body circumferentially, spaced apart by an angle;

(m) wherein, a second group of two of the one or more support members, when in their support configuration, extend away from the longitudinal axis of the catheter body by an angle relative to each other that is less than 180°; and (n) wherein, owing to: (i) the attachment of the catheter body to the distal ends of the one or more support members, (ii) the entering of the one or more support members into the one or more elongated, tubular inner lumina inside the catheter body, and (iii) the one or more support members having the hydrophilic surface and being made entirely or in part of metal or metal alloy, the second group of two support members, when exposed to external forces, radially extend from the catheter body circumferentially, spaced apart by an angle.

* * * * *